(12) United States Patent
Mihalik

(10) Patent No.: US 6,207,179 B1
(45) Date of Patent: Mar. 27, 2001

(54) PARASITICIDAL FORMULATION FOR ANIMALS AND A METHOD OF MAKING THIS FORMULATION

(75) Inventor: Richard Mihalik, St. Joseph, MO (US)

(73) Assignee: Phoenix Scientific, Inc., St. Joseph, MO (US)

( * ) Notice: Subject to any disclaimer, the term of this patent is extended or adjusted under 35 U.S.C. 154(b) by 0 days.

(21) Appl. No.: 09/573,513

(22) Filed: May 18, 2000

(51) Int. Cl.$^7$ .......................... A01N 25/00; A01N 43/54
(52) U.S. Cl. ............................... 424/405; 514/256
(58) Field of Search ............... 424/405; 514/256

(56) References Cited

U.S. PATENT DOCUMENTS

| | | | |
|---|---|---|---|
| 4,438,258 | * 3/1984 | Graham | 528/361 |
| 4,624,945 | 11/1986 | Eckenhoff et al. | 514/30 |
| 5,824,653 | 10/1998 | Beuvry et al. | 514/30 |
| 6,025,357 | * 2/2000 | Kalbe et al. | 514/250 |

FOREIGN PATENT DOCUMENTS

| | | |
|---|---|---|
| 187012 | * 7/1986 | (EP) . |
| 11043408 | * 2/1999 | (JP) . |
| WO 95/05181 | 2/1995 | (WO) . |

OTHER PUBLICATIONS

Reinemeyer, C., "Anoplocephala Perfoliata Infection of Equids," pp. 1–13.

* cited by examiner

*Primary Examiner*—Jose' G. Dees
*Assistant Examiner*—Alton Pryor
(74) *Attorney, Agent, or Firm*—Shook, Hardy & Bacon LLP

(57) ABSTRACT

A formulation for treating and preventing parasite infestations in horses, dogs, cats, and other animals is provided. This formulation includes a mixture of an edible non-aqueous liquid, a thickening agent, an agent effective against nematodes and obligate parasitic flies and a cestocidal agent, wherein the cestocidal agent is pyrantel, morantel, any salt thereof, or any combination thereof. Preferably, the agent effective against nematodes and obligate parasitic flies is an avermectin, a milbemycin or any combination thereof. Another aspect of the present invention is a method of making this parasiticidal formulation. A further aspect of the present invention is a method for administering the parasiticidal formulation of the present invention to an animal in the form of a paste.

6 Claims, No Drawings

PARASITICIDAL FORMULATION FOR ANIMALS AND A METHOD OF MAKING THIS FORMULATION

STATEMENT REGARDING FEDERALLY SPONSORED RESEARCH OR DEVELOPMENT

Not applicable.

CROSS-REFERENCE TO RELATED APPLICATIONS

Not applicable.

BACKGROUND OF THE INVENTION

The present invention relates to a formulation for treating, controlling and preventing parasitic worm infestations and a method for making the formulation. More specifically, the present invention relates to a combination roundworm and tapeworm parasiticide for use in horses and household pets.

Several types of parasites, including cestodes, nematodes and obligate parasitic insects, particularly flies, commonly plague horses, dogs and cats. Cestodes are flatworms and include, for example, tapeworms, while nematodes are roundworms. Avermectins and milbemycins are nematocidal agents commonly used in the treatment and control of parasitic roundworm infestations in equines, including domestic horses, donkeys, mules and zebras, as well as in companion animals, namely cats and dogs. These agents are also effective against obligate parasitic flies. Contrary to popular belief among animal owners, however, these agents are ineffective against tapeworm infestations. Rather, tapeworm infestations must be controlled and treated by a cestocidal agent.

Studies have shown that misinformation about tapeworm treatment and control is common among horse owners. Many horse owners evidently believe that ivermectin, an avermectin used for treating and controlling roundworm infestations, is effective in controlling tapeworm infestations as well. This misinformation may account for a rise in the prevalence of certain tapeworms. A particular equine tapeworm whose prevalence is on the rise is *Anoplocephala perfoliata*.

Tapeworms are pervasive parasites that appear to infect at least half of all mature horses. Post-mortem studies have shown that, in general, at least 50% of mature horses in many populations are infected with *A. perfoliata*. *A. perfoliata* is a type of tapeworm that can infect all types of equine animals. Adult *A. perfoliata* attach to the posterior regions of the equine intestinal tract. The highest concentration is in the cecal wall but a fair amount attach to the terminal ilium and ventral colon as well. The greatest concentration of *A. perfoliata*, and thus the greatest associated damage, occurs at the ileocecal junction. *A. perfoliata* infestation increases the incidence of spasmodic colon and ileal impaction in horses. Tapeworms also have been implicated as a cause of cecal and ileocecal intussusceptions in young horses. The latter conditions are potentially fatal and can be remedied only by complicated and expensive abdominal surgery.

There are only a few classes of drugs which are effective in the treatment, control and prevention of tapeworm infestations. Among these classes are praziquantel, pyrantel and morantel compounds. Parasiticidal formulations have been disclosed which contain praziquantel combined with a variety of roundworm controlling agents. One such formulation is disclosed in U.S. Pat. No. 5,824,653 to Beuvry et al. The compounds which result from these combinations, however, may be dangerous as praziquantel has been shown to be toxic at levels other than low dosages. Additionally, praziquantel purportedly is bitter to taste making it unpalatable and thus undesirable in ingestable formulations, for example, pastes.

Pyrantel and morantel compounds are currently believed by those skilled in the art to offer an inadequate substitute to praziquantel in the treatment and control of tapeworm infestations. Pyrantel salts generally either are only partially effective against tapeworms at their label dosages (e.g., pyrantel pamoate) or must be administered in daily regimes (e.g., pyrantel tartrate). Further, pyrantel pamoate offers a low suspended solids content when in paste form, the highest percentage encountered being about 43.95% weight per weight (w/w). A paste with a low suspended solids content contains less active ingredient per unit than a paste with a higher suspended solids content. Therefore, a higher volume of paste must be delivered to the animal in order to achieve the same therapeutic effect.

Accordingly, there remains a need in the veterinary industry for a combination parasiticidal formulation containing both a cestocidal agent and an agent effective against nematodes and obligate parasitic flies that is less toxic than formulations containing praziquantel. Further, a palatable combination parasiticide is needed for administration in ingestable forms. The primary objective of this invention is to meet these needs.

SUMMARY OF THE INVENTION

Accordingly, it is an object of the present invention to provide a parasiticidal formulation that contains at least one agent effective against nematodes and obligate parasitic flies and at least one agent effective against cestodes so as to broaden the formulation's spectrum of parasite protection.

It is another object of the present invention to provide a combination parasiticidal formulation containing at least one agent that is effective against nematodes and obligate parasitic flies and at least one agent that is effective against cestodes which is less toxic than prior formulations which include praziquantel.

A further object of the present invention is to provide a palatable parasiticidal formulation that contains at least one agent that is effective against nematodes and obligate parasitic flies and at least one agent that is effective against cestodes which may be administered as a paste.

Still another object of the present invention is to provide a method of making a parasiticidal formulation that achieves the foregoing objects.

Yet another object of the present invention is to provide a method for administering a parasiticidal formulation that achieves the foregoing objects.

According to the present invention, the foregoing and other objects are achieved by a parasiticidal formulation that includes a mixture of an edible non-aqueous liquid, a thickening agent, an agent effective against nematodes and obligate parasitic flies and an agent effective against cestodes, wherein the cestocidal agent is pyrantel, morantel, any salt thereof, or any combination thereof. Preferably, the agent effective against nematodes and obligate parasitic flies is an avermectin, a milbemycin, a derivative thereof, or any combination thereof. Another aspect of the present invention is a method of making this parasiticidal formulation. This method includes mixing the above-mentioned components. A further aspect of the present invention is a method for administering the parasiticidal formulation of the present invention to an animal. This method of administration includes providing the parasiticidal formulation described above in the form of a paste and administering it to an animal for ingestion.

Additional objects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF THE PREFERRED EMBODIMENT

The parasiticidal formulation of the present invention is an effective ingestable formulation for the treatment and control of cestode, nematode and obligate parasitic fly infestations in equine and companion animals. Such animals include, but are not limited to, horses, donkeys, mules, zebras, dogs and cats. The formulation includes an edible, non-aqueous liquid, a thickening agent, an agent for treating and controlling roundworm and obligate parasitic fly infestations and a cestocidal agent for treating and controlling tapeworm infestations. This mixture provides a unique formulation in which the agent effective against nematodes and obligate parasitic flies is allowed to dissolve substantially into solution while the cestocidal agent remains generally suspended. Thus, the system allows for delivery of two different parasiticidal agents in two different physical states simultaneously in a single oral formulation.

The cestocidal agent of the present invention includes pyrantel, morantel, any salt of pyrantel or morantel, or any combination thereof. These compounds offer advantages over praziquantel in the control and treatment of tapeworm infestations in that they have a higher dosage safety margin than praziquantel. Pyrantel pamoate, a salt of pyrantel, for example, should present little to no adverse reaction when ingested by horses in a concentration equivalent to two to five times the label recommended dosage. Further, pyrantels are desirable because horse owners are familiar with this group of compounds. Additionally, pyrantel and morantel are more palatable than praziquantel as these compounds do not share the bitter taste associated with praziquantel.

Preferably, the cestocidal agent of the present invention is a salt of pyrantel. Pyrantel salts that may be used in the formulation of the present invention include, but are not limited to, pyrantel pamoate, pyrantel tartrate or any combination thereof. Preferably, the cestocidal agent of the present invention is pyrantel pamoate. Pyrantel pamoate, at sufficiently high dosages, eliminates and controls infestations by a variety of tapeworms, including *Anoplocephala perfoliata*.

Pyrantel pamoate usually is classified as a nematocidal agent rather than a cestocidal agent at its recommended label dosage of about 6.6 milligrams per kilogram of animal. At this dosage, pyrantel pamoate has only partial activity in the treatment and control of tapeworm infestations. Effectiveness percentages from about 65% to 100% against cestode infestations have been shown with paste formulations, the average being about 85% efficacy. However, at about twice the label recommended dosage or higher, pyrantel pamoate exhibits tapeworm controlling activity unattainable by many cestocidal compounds at any dosage. It has been observed that at an elevated dosage of about two times the label recommended dosage, or about 13.2 milligrams per kilogram of animal, pyrantel pamoate exhibits between about 93% and 97.8% efficacy in horses infected with *A. perfoliata*. At an elevated dosage of about three times the label recommended dosage, or about 19.8 milligrams per kilogram of animal, pyrantel pamoate is about 100% effective in treating cestode infestations. Consequently, the parasiticidal formulation of the present invention includes concentrations of pyrantel pamoate at about two to three times the dosage recommended for treatment and control of roundworm infestations.

When the cestocidal agent chosen is pyrantel pamoate, the formulation of the present invention preferably may include about 40–75% w/w pyrantel pamoate (a total of about 14–26% w/w pyrantel in the formulation). More preferably, the formulation of the present invention may include about 50–65% w/w pyrantel pamoate (a total of about 17–23% w/w pyrantel in the formulation). Formulations containing other cestocidal agents besides pyrantel pamoate are also contemplated by this invention, as discussed above. If a different pyrantel compound is used, preferably the formulation would contain pyrantel in an amount similar to the amounts discussed above.

The agents which are effective against nematodes and obligate parasitic flies that may be used in the formulation of the present invention include, but are not limited to, avermectins, milbemycins, any derivative thereof, or any combination thereof. Avermectins that may be used in the formulation of the present invention include, but are not limited to, abamectin, doramectin, eprinomectin, ivermectin, moxidectin, selamectin, or any combination thereof. These agents are most effective when substantially dissolved in solution, i.e., when at least about 90% of the agent present is dissolved. Thus, it is preferred that these agents be combined with a solvent before being administered to an animal. Preferably the agent used in the formulation of the present invention is ivermectin. Ivermectin kills a variety of roundworms including stomach worms, intestinal worms, lungworms, barber's pole worms, lice and mites, as well as bots and grubs of obligate parasitic flies.

When the agent chosen is ivermectin, the formulation of the present invention preferably may include about 0.10–10% w/w ivermectin. More preferably, the formulation of the present invention may include about 0.25–0.35% w/w ivermectin.

As noted, cestocidal agents and agents effective against nematodes and obligate parasitic flies each provide protection against different species of parasites. Thus, when combined in a single parasiticidal formulation, the formulation provides protection against a broader spectrum of parasites than a formulation containing either parasiticidal agent alone. The formulation of the present invention preferably may include a total of about 45–70% w/w parasiticidal agent, achieved by combining an agent effective against nematodes and obligate parasitic flies and a cestocidal agent. More preferably, the formulation of the present invention includes about 50–60% w/w parasiticidal agents.

When using ivermectin and pyrantel pamoate in combination, the parasiticidal formulation of the present invention preferably may include about 0.2–1.0% w/w ivermectin and about 45–65% w/w pyrantel pamoate. More preferably, the formulation of the present invention may include about 0.2–0.5% w/w ivermectin and about 50–60% w/w pyrantel pamoate.

The edible, non-aqueous liquid that may be used in the formulation of the present invention includes, but is not limited to, edible glycol polymers, edible oils, or any combination thereof. Edible glycol polymers that may be used in the formulation of the present invention include, but are not limited to, propylene glycol, polyethylene glycol, glycerine (glycerol), glycerol formal, or any combination thereof. Edible oils that may be used in the formulation of the present invention include, but are not limited to, Arachis oil (peanut oil), polyoxyl castor oils, soybean oil, or any combination thereof. Preferably, the edible, non-aqueous liquid is propylene glycol.

The edible, non-aqueous liquid preferably is present in the parasiticidal formulation of the present invention in an amount effective, in combination with the thickening agent, for substantially dissolving a therapeutic amount of one or more agents effective against nematodes and obligate parasitic flies while allowing one or more cestocidal agents to remain generally suspended. The agents effective against nematodes and obligate parasitic flies are substantially dissolved in solution when at least about 90% of the agent present is dissolved. Cestocidal agents are generally suspended when less than about 10% of the agent present is dissolved. The formulation of the present invention preferably may include a total of about 40–50% w/w edible, non-aqueous liquid. More preferably, the formulation of the present invention may include about 42–46% w/w edible, non-aqueous liquid.

The thickening agent that may be used in the formulation of the present invention includes, but is not limited to, carbomers, cornstarch, polyethylene, polyvinylpyrrolidones, edible clay, xanthan gum, or any combination thereof. Preferably, the thickening agents are a carbomer and xanthan gum. A suitable carbomer is Carbomer 974P manufactured by B.F. Goodrich. The thickening agent preferably includes an amount that is effective, in combination with the edible, non-aqueous liquid, to substantially dissolve a therapeutic amount of one or more agents effective against nematodes and obligate parasitic flies (preferably at least about 90% dissolved) while allowing one or more cestocidal agents to remain generally suspended (preferably less than about 10% dissolved). The formulation of the present invention preferably may include about 0.01–1.0% w/w thickening agent. More preferably, the formulation of the present invention may include about 0.09–65% w/w thickening agent.

The combination of an edible, non-aqueous liquid and a thickening agent to form the unique system of the present invention allows one or more cestocidal agents to dissolve substantially while allowing one or more agents effective against nematodes and obligate parasitic flies to remain generally suspended. As a result, the system of the present invention allows for delivery of two different parasiticidal agents in two different physical states simultaneously in a single oral formulation. The combination of the edible, non-aqueous liquid and the thickening agent also functions to transport one or more cestocidal agents and one or more agents effective against nematodes and obligate parasitic flies into an animal in the physical state in which each is most effective so that the agents may interact therapeutically with parasites in the animal. In animals with no parasite infestations upon administration, the combination of the edible, non-aqueous liquid and the thickening agent functions to transport one or more cestocidal agents and one or more agents effective against nematodes and obligate parasitic flies into an animal in the physical state in which each is most effective so that the animal is protected from subsequent infestations by certain parasites.

Further, the formulation of the present invention allows for higher suspended solids content for some cestocidal agents than was foreseen as being possible from the prior art. For example, the formulation of the present invention allows for a paste containing pyrantel pamoate having a suspended solids content of up to about 70% w/w, with a preferred concentration of about 54.13% w/w. The highest concentration previously encountered in a paste containing pyrantel was about 43.95% w/w. The higher suspended solids content allows for a significantly smaller volume of paste to be administered, making it easier to deliver higher dosages of pyrantel than when previously available formulations are used.

As discussed above, cestocidal agents and agents effective against nematodes and obligate parasitic flies each provide protection against different species of parasites. Thus, when a cestocidal agent and an agent effective against nematodes and obligate parasitic flies are combined in a single parasiticidal formulation, the formulation provides protection against a broader spectrum of parasites than a formulation containing either parasiticidal agent alone. The parasiticidal formulation of the present invention may be administered either to treat infected animals or to prevent infestations in non-infected animals. Preferably, the formulation is administered once per month.

While the edible, non-aqueous liquid, thickening agent, cestocidal agent and agent effective against nematodes and obligate parasitic flies are the only components necessary in the formulation of the present invention, a number of optional ingredients may be added to enhance certain properties of the formulation. One such optional ingredient is a preservative which acts to preserve both parasiticidal agents in the physical state in which they are most effective. Preservatives that may be used in the formulation of the present invention include, but are not limited to, methylparaben, propylparaben, or any combination thereof. Preferably, the formulation of the present invention includes a combination of methylparaben and propylparaben in a ratio of approximately 10:1 respectively. If a combination of methylparaben and propylparaben is chosen as a preservative for the formulation, the parasiticidal formulation of the present invention preferably may include about 0.15–0.25% w/w methylparaben and about 0.015–0.025% w/w propylparaben. More preferably, the parasiticidal formulation of the present invention may include about 0.18% w/w methylparaben and about 0.02% w/w propylparaben.

Another optional ingredient that may be included in the formulation of the present invention is an additional solvent for the agent effective against nematodes and obligate parasitic flies. Preferably this solvent is water. Water may be present in a concentration ranging from about 0–10% w/w depending upon the concentration of edible, non-aqueous liquid used. The total amount of solvent should be sufficient to dissolve substantially all of the agent effective against nematodes and obligate parasitic flies present in the formulation of the present invention while allowing all of the cestocidal agent to remain generally suspended.

One preferred formulation of the present invention includes pyrantel pamoate, ivermectin, xanthan gum, carbomer, methylparaben, propylparaben and propylene glycol. Another preferred formulation of the present invention includes pyrantel pamoate, ivermectin, xanthan gum, carbomer and propylene glycol. A highly preferred formulation of the present invention which includes a preservative is described in Example 1. A highly preferred formulation of the present invention which does not include a preservative is described in Example 2.

The parasiticidal formulation of the present invention is made by combining an edible non-aqueous liquid, a thickening agent, an agent effective against nematodes and obligate parasitic flies and a cestocidal agent to form a mixture. Preferably, ivermectin and pyrantel pamoate may be used respectively. The order in which components are added in making the formulation is not critical. The formulation may optionally be heated to between about 60° and 80° C., continuously or intermittently, during its preparation in order to dissolve the agent effective against nematodes and obligate parasitic flies more quickly. This process can be scaled to make any desired quantity of the formulation.

One preferred method of making the parasiticidal formulation of the present invention includes placing a quantity of edible, non-aqueous liquid in a vessel and warming it to about 70° C. Next, a quantity of an agent effective against nematodes and obligate parasitic flies is added, and the resulting solution is cooled to room temperature. The cestocidal agent is then added and mixed with the solution for an effective period of time. The cestocidal agent will not dissolve into solution but instead will remain generally suspended throughout, i.e., less than about 10% will dissolve. A thickening agent is then added and mixed into the solution until it dissolves substantially, i.e., until at least 90% of the thickening agent present is dissolved. Optionally, a preservative then may be added and mixed into the solution until substantially dissolved, i.e., until at least 90% of the preservative present is dissolved.

Preferably, the parasiticidal formulation of the present invention is administered as a paste formulation to any equine or companion animal. It is particularly useful for domestic horses, donkeys, mules, zebras, cats and dogs. Preferably, the paste is ingested by the animal and is administered in a dosage of about 65–75 milligrams per kilogram of animal once per month.

The following are examples of various parasiticidal formulations and methods of making these formulations that are within the scope of this invention. These examples are not meant in any way to limit the scope of this invention.

EXAMPLE 1

Propylene glycol, in a quantity amounting to 44.17% w/w of the final formulation, was added to a vessel and warmed to 70° C. Agitation began. With continued agitation, a quantity of ivermectin amounting to 0.29% w/w of the final formulation was added to the propylene glycol and mixed with it until all of the ivermectin substantially dissolved. The resulting solution was then cooled to room temperature. A quantity of pyrantel pamoate amounting to 55.14% w/w of the final formulation (19.13% w/w of final formulation as pyrantel) was then added and mixed with the solution. The pyrantel pamoate did not dissolve in the solution but instead remained generally suspended throughout. Next, a quantity of xanthan gum amounting to 0.18% w/w of the final formulation was added to the mixture. With continued agitation, Carbomer 974P was added to the mixture in a quantity amounting to 0.02% w/w of the final formulation. Subsequently, methylparaben, in a quantity amounting to 0.18% w/w of the final formulation, was added to the mixture, followed by a quantity of propylparaben amounting to 0.02% w/w of the final formulation. The resulting formulation is within the scope of the present invention and includes two parasiticidal agents, each targeting different species of parasites.

EXAMPLE 2

Propylene glycol, in a quantity amounting to 44.37% w/w of the final formulation, was added to a vessel and warmed to 70° C. Agitation began. With continued agitation, a quantity of ivermectin amounting to 0.29% w/w of the final formulation was added to the propylene glycol and mixed with it until all of the ivermectin substantially dissolved. The resulting solution was then cooled to room temperature. A quantity of pyrantel pamoate amounting to 55.14% w/w of the final formulation (19.13% w/w of final formulation as pyrantel) was then added and mixed with the solution. The pyrantel pamoate did not dissolve in the solution but instead remained generally suspended throughout. With continued agitation, a quantity of xanthan gum amounting to 0.18% w/w of the final formulation was added to the mixture. Subsequently, carbomer 974P was added to the mixture in a quantity amounting to 0.02% w/w of the final formulation. The resulting formulation is within the scope of the present invention and includes two parasiticidal agents, each targeting different species of parasites.

EXAMPLE 3

Propylene glycol, in a quantity amounting to 30% w/w of the final formulation, was added to a vessel and warmed to 70° C. Agitation began. With continued agitation, water in a quantity amounting to 7.285% w/w of the final formulation, was added to the propylene glycol to form a solution. Next, a quantity of ivermectin amounting to 0.325% w/w of the final formulation was added to the solution and mixed with it until all of the ivermectin substantially dissolved. The resulting solution was then cooled to room temperature. A quantity of pyrantel pamoate amounting to 61.74% w/w of the final formulation (21.42% w/w of final formulation as pyrantel) was then added and mixed with the solution. The pyrantel pamoate did not dissolve in the solution but instead remained generally suspended throughout. Lastly, a quantity of xanthan gum amounting to 0.65% w/w of the final formulation was added to the mixture. The resulting formulation is within the scope of the present invention and includes two parasiticidal agents, each targeting different species of parasites.

EXAMPLE 4

Propylene glycol, in a quantity amounting to 28% w/w of the final formulation, was added to a vessel and warmed to 70° C. Agitation began. With continued agitation, water, in a quantity amounting to 9.285% w/w of the final formulation, was added to the propylene glycol to form a solution. Next, ivermectin amounting to 0.325% w/w of the final formulation was added to the solution and mixed with it until all of the ivermectin substantially dissolved. The resulting solution was then cooled to room temperature. A quantity of pyrantel pamoate amounting to 61.74% w/w of the final formulation (21.42% w/w of final formulation as pyrantel) was then added and mixed with the solution. The pyrantel pamoate did not dissolve in the solution but instead remained generally suspended throughout. Lastly, a quantity of xanthan gum amounting to 0.65% w/w of the final formulation was added to the mixture. The resulting formulation is within the scope of the present invention and includes two parasiticidal agents, each targeting different species of parasites.

EXAMPLE 5

Propylene glycol, in a quantity amounting to 32.0% w/w of the final formulation, was added to a vessel and warmed to 70° C. Agitation began. With continued agitation, water, in a quantity amounting to 5.285% w/w of the final formulation, was added to the propylene glycol to form a solution. Next, ivermectin amounting to 0.325% w/w of the final formulation was added to the solution and mixed with it until all of the ivermectin substantially dissolved. The resulting solution was then cooled to room temperature. A quantity of pyrantel pamoate amounting to 61.74% w/w of the final formulation (21.42% w/w of final formulation as pyrantel) was then added and mixed with the solution. The pyrantel pamoate did not dissolve in the solution but instead remained generally suspended throughout. Lastly, a quantity of xanthan gum amounting to 0.65% w/w of the final formulation was added to the mixture. The resulting formulation is within the scope of the present invention and includes two parasiticidal agents, each targeting different species of parasites.

EXAMPLE 6

Propylene glycol, in a quantity amounting to 37.836% w/w of the final formulation, was added to a vessel and warmed to 70° C. Agitation began. With continued agitation, water, in a quantity amounting to 7.0% w/w of the final formulation, was added to the propylene glycol to form a solution. Next, ivermectin amounting to 0.284% w/w of the final formulation was added to the solution and mixed with it until all of the ivermectin substantially dissolved. The resulting solution was then cooled to room temperature. A quantity of pyrantel pamoate amounting to 54.03% w/w of the final formulation (18.75% w/w of final formulation as pyrantel) was then added and mixed with the solution. The pyrantel pamoate did not dissolve in the solution but instead remained generally suspended throughout. With continued agitation, a quantity of xanthan gum amounting to 0.65% w/w of the final formulation was added to the mixture. Lastly, Carbomer 974P was added to the mixture in a quantity amounting to 0.02% w/w of the final formulation. The resulting formulation is within the scope of the present invention and includes two parasiticidal agents, each targeting different species of parasites.

EXAMPLE 7

Propylene glycol, in a quantity amounting to 44.806% w/w of the final formulation, was added to a vessel and warmed to 70° C. Agitation began. With continued agitation, water, in a quantity amounting to 0.48% w/w of the final formulation, was added to the propylene glycol to form a solution. Next, ivermectin amounting to 0.284% w/w of the final formulation was added to the solution and mixed with it until all of the ivermectin substantially dissolved. The resulting solution was then cooled to room temperature. With continued agitation, a quantity of pyrantel pamoate amounting to 54.03% w/w of the final formulation (18.75% w/w of final formulation as pyrantel) was then added and mixed with the solution. The pyrantel pamoate did not dissolve in the solution but instead remained generally suspended throughout. Next, a quantity of xanthan gum amounting to 0.2% w/w of the final formulation was added to the mixture. Lastly, Carbomer 974P was added to the mixture in a quantity amounting to 0.2% w/w of the final formulation. The resulting formulation is within the scope of the present invention and includes two parasiticidal agents, each targeting different species of parasites.

EXAMPLE 8

Propylene glycol, in a quantity amounting to 43.4% w/w of the final formulation, was added to a vessel and warmed to 70° C. Agitation began. With continued agitation, a quantity of ivermectin amounting to 0.275% w/w of the final formulation was added to the propylene glycol and mixed with it until all of the ivermectin substantially dissolved. The resulting solution was then cooled to room temperature. A quantity of pyrantel pamoate amounting to 56.17% w/w of the final formulation (19.49% w/w of final formulation as pyrantel) was then added and mixed with the solution. The pyrantel pamoate did not dissolve in the solution but instead remained generally suspended throughout. With continued agitation, a quantity of xanthan gum amounting to 0.097% w/w of the final formulation was added to the mixture. Lastly, Carbomer 974P was added to the mixture in a quantity amounting to 0.097% w/w of the final formulation. The resulting formulation is within the scope of the present invention and includes two parasiticidal agents, each targeting different species of parasites.

EXAMPLE 9

Propylene glycol, in a quantity amounting to 44.14% w/w of the final formulation, was added to a vessel and warmed to 70° C. Agitation began. With continued agitation, a quantity of ivermectin amounting to 0.29% w/w of the final formulation was added to the propylene glycol and mixed with it until all of the ivermectin substantially dissolved. The resulting solution was then cooled to room temperature. A quantity of pyrantel pamoate amounting to 55.17% w/w of the final formulation (19.14% w/w of final formulation as pyrantel) was then added and mixed with the solution. The pyrantel pamoate did not dissolve in the solution but instead remained generally suspended throughout. Next, a quantity of xanthan gum amounting to 0.1% w/w of the final formulation was added to the mixture. With continued agitation, Carbomer 974P was added to the mixture in a quantity amounting to 0.1% w/w of the final formulation. Subsequently, methylparaben, in a quantity amounting to 0.18% w/w of the final formulation, was added to the mixture, followed by a quantity of propylparaben amounting to 0.02% w/w of the final formulation. The resulting formulation is within the scope of the present invention and includes two parasiticidal agents, each targeting different species of parasites.

EXAMPLE 10

Propylene glycol, in a quantity amounting to 49.705% w/w of the final formulation, was added to a vessel and warmed to 70° C. Agitation began. With continued agitation, a quantity of ivermectin amounting to 0.235% w/w of the final formulation was added to the propylene glycol and mixed with it until all of the ivermectin substantially dissolved. The resulting solution was then cooled to room temperature. A quantity of pyrantel pamoate amounting to 49.7% w/w of the final formulation (17.25% w/w of final formulation as pyrantel) was then added and mixed with the solution. The pyrantel pamoate did not dissolve in the solution but instead remained generally suspended throughout. Next, a quantity of xanthan gum amounting to 0.135% w/w of the final formulation was added to the mixture. With continued agitation, Carbomer 974P was added to the mixture in a quantity amounting to 0.045% w/w of the final formulation. Subsequently, methylparaben, in a quantity amounting to 0.162% w/w of the final formulation, was added to the mixture, followed by a quantity of propylparaben amounting to 0.018% w/w of the final formulation. The resulting formulation is within the scope of the present invention and includes two parasiticidal agents, each targeting different species of parasites.

EXAMPLE 11

Propylene glycol, in a quantity amounting to 38.199% w/w of the final formulation, was added to a vessel and warmed to 70° C. Agitation began. With continued agitation, a quantity of sterile water in a quantity amounting to 6.0% w/w of the final formulation was added to the propylene glycol to form a solution. Next, ivermectin amounting to 0.261% w/w of the final formulation was added to the solution and mixed with it until all of the ivermectin substantially dissolved. The resulting solution was then cooled to room temperature. A quantity of pyrantel pamoate amounting to 55.14% w/w of the final formulation (19.13% w/w of final formulation as pyrantel) was then added and mixed with the solution. The pyrantel pamoate did not dissolve in the solution but instead remained generally suspended throughout. With continued agitation, a quantity of xanthan gum amounting to 0.1% w/w of the final formulation was added to the mixture. With continued agitation, a quantity of Carbomer 974P was added to the mixture in a quantity amounting to 0.1% w/w of the final formulation. Lastly, methylparaben, in a quantity amounting to 0.18% w/w of the final formulation, was added to the mixture, followed by a quantity of propylparaben amounting to 0.02% w/w of the final formulation. The resulting formulation is within the scope of the present invention and includes two parasiticidal agents, each targeting different species of parasites.

EXAMPLE 12

Propylene glycol, in a quantity amounting to 44.19% w/w of the final formulation, was added to a vessel and warmed to 70° C. Agitation began. With continued agitation, a quantity of ivermectin amounting to 0.261% w/w of the final formulation was added to the propylene glycol and mixed with it until all of the ivermectin substantially dissolved. The resulting solution was then cooled to room temperature. A quantity of pyrantel pamoate amounting to 55.14% w/w of the final formulation (19.13% w/w of final formulation as pyrantel) was then added and mixed with the solution. The pyrantel pamoate did not dissolve in the solution but instead remained generally suspended throughout. Next, a quantity of xanthan gum amounting to 0.15% w/w of the final formulation was added to the mixture. With continued agitation, Carbomer 974P was added to the mixture in a quantity amounting to 0.05% w/w of the final formulation. Lastly, methylparaben, in a quantity amounting to 0.18% w/w of the final formulation, was added to the mixture, followed by a quantity of propylparaben amounting to 0.02% w/w of the final formulation. The resulting formulation is within the scope of the present invention and includes two parasiticidal agents, each targeting different species of parasites.

From the foregoing, it will be seen that this invention is one that is well adapted to attain all the ends and objects hereinabove set forth together with other advantages which are obvious and inherent to the formulation.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth is to be interpreted as illustrative and not in a limiting sense.

Having thus described my invention, I claim:

1. A parasiticidal formulation, comprising the mixture of:
   an edible, non-aqueous liquid that is an edible oil selected from the group consisting of Arachis oil, polyoxyl castor oil, soybean oil and any combination thereof;
   a thickening agent;
   an agent effective against nematodes and obligate parasitic flies; and
   a cestocidal agent, wherein said cestocidal agent is selected from the group consisting of pyrantel, morantel, any salt thereof and any combination thereof.

2. A parasiticidal formulation, comprising the mixture of:
   an edible, non-aqueous liquid that is an edible glycol polymer selected from the group consisting of propylene glycol, polyethylene glycol, glycerine, glycerol formal and any combination thereof, wherein said non-aqueous liquid is comprised of about 25–55% weight per weight propylene glycol;
   a thickening agent;
   an agent effective against nematodes and obligate parasitic flies; and
   a cestocidal agent, wherein said cestocidal agent is selected from the group consisting of pyrantel, morantel, any salt thereof and any combination thereof.

3. A parasiticidal formulation, comprising the mixture of:
   an edible, non-aqueous liquid;
   a thickening agent selected from the group consisting of a carbomer, cornstarch, polyethylene, a polyvinylpyrrolidone, an edible clay, xanthan gum and any combination thereof;
   an agent effective against nematodes and obligate parasitic flies; and
   a cestocidal agent, wherein said cestocidal agent is selected from the group consisting of pyrantel, morantel, any salt thereof and any combination thereof.

4. The formulation of claim 3, wherein said thickening agent is comprised of a carbomer and xanthan gum.

5. The formulation of claim 4, wherein said formulation is comprised of about 0.01–0.5% weight per weight carbomer and about 0.05–1.0% weight per weight xanthan gum.

6. A parasiticidal formulation, comprising the mixture of:
   an edible, non-aqueous liquid;
   a thickening agent;
   an agent effective against nematodes and obligate parasitic flies;
   a cestocidal agent, wherein said cestocidal agent is selected from the group consisting of pyrantel, morantel, any salt thereof and any combination thereof; and
   a preservative selected from the group consisting of methylparaben, propylparaben and any combination thereof.

* * * * *